United States Patent [19]

Borst

[11] 4,445,857
[45] May 1, 1984

[54] DENTAL CAVITY MEASURING INSTRUMENT

[75] Inventor: Arnoldus J. Borst, Waalwijk, Netherlands

[73] Assignee: Stichting Kennisexploitatie Nederland, Driebergen-Rijsenburg, Netherlands

[21] Appl. No.: 355,365

[22] Filed: Mar. 8, 1982

[30] Foreign Application Priority Data

Mar. 16, 1981 [NL] Netherlands ........................ 8101279

[51] Int. Cl.³ ................................................ A61C 3/00
[52] U.S. Cl. ..................................... 433/75; 33/174 D
[58] Field of Search ........................... 433/72, 75, 141; 128/776, 777; 33/174 D, 169 B, 171

[56] References Cited

U.S. PATENT DOCUMENTS

| | | | |
|---|---|---|---|
| 2,545,881 | 3/1951 | Graham | 33/171 |
| 2,787,837 | 4/1957 | Gelfand | 433/72 |
| 4,141,345 | 2/1979 | Allen et al. | 33/174 D |
| 4,203,223 | 5/1980 | Lautenschlager et al. | 433/75 |
| 4,340,069 | 7/1982 | Yeaple | 433/72 |

FOREIGN PATENT DOCUMENTS 7703431 10/1978 Netherlands ........................ 433/72

OTHER PUBLICATIONS

"A Simple Constant-Force Pocket Probe", Borsbroom et al., pp. 390-391, vol. 52, No. 7.

Primary Examiner—John J. Wilson
Attorney, Agent, or Firm—J. David Dainow

[57] ABSTRACT

An instrument for measuring the depth of a periodontal pocket cavity including a probe needle, a needle holder and a handle, has a hinge construction whereby the needle with the needle holder is pivotable relative to the handle against the action of a bias spring which has a flat spring characteristic within the restricted pivoting range of the hinge.

6 Claims, 6 Drawing Figures

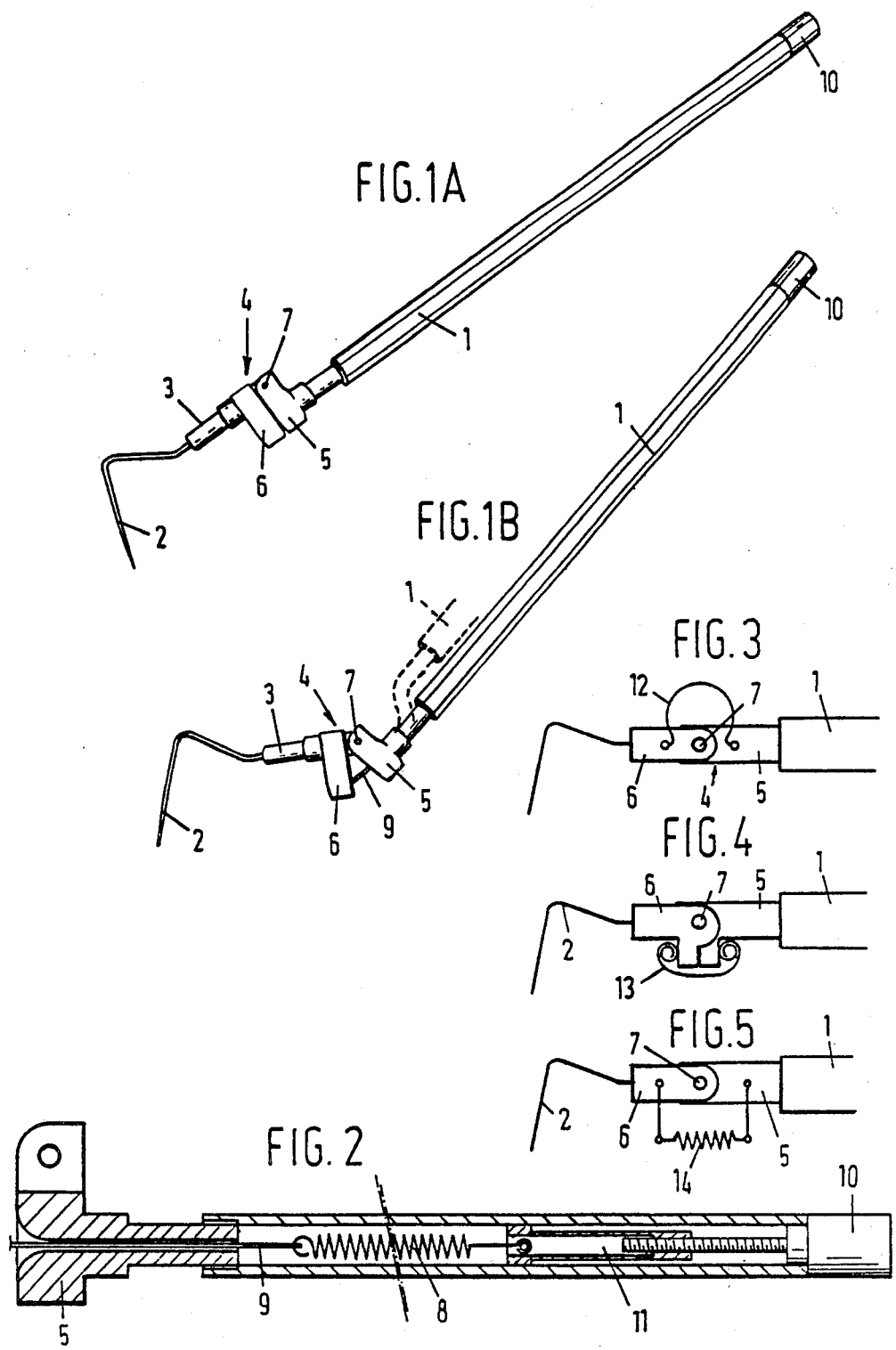

DENTAL CAVITY MEASURING INSTRUMENT

BACKGROUND OF THE INVENTION

The invention relates to a measuring instrument for the depth of the periodontal cavity, comprising a probe needle, a needle holder and a handle, wherein the needle with the needle holder is restrictedly movable from a start position determined by an abutment against the action of a bias spring, the deformation of which caused by the needle movement causes no substantial change of the spring force.

For measuring the periodontal cavity the dentists generally use a measuring instrument consisting of a handle with a holder for a probe needle fixedly attached thereto. It will be clear that the pocket depth thus measured is highly dependent on the probe force applied by the user of the instrument and, therefore, the measuring accuracy at such rigid instruments is low just as the reproduceability of the measurements.

Earlier proposals for a measuring instrument for the depth of the periodontal cavity with a constant adjustable probe force relate to extensive and/or voluminous constructions, such as electronic pressure registration apparatus and complex spring constructions. A measuring instrument for the depth of the periodontal cavity of the last-mentioned type comprises a handle to which a frame is attached, in which frame two shafts extend transverse to the center line of the handle. A bushing is mounted on each of the shafts and a long leaf spring is wound on the two bushings in mutually opposite directions over the respective bushings. This construction is known as a spring motor of the Tensator type, wherein by rotation of one of the bushings the spring wound thereon is unwound and is wound on the other bushing or vice versa, and wherein a constant torque is transferred. In this manner a bias force can be applied in such a manner that as soon as, during the use of the instrument, a force with a value in the order of magnitude of 15 g (0.15 N) is applied at the needle tip, the needle holder borne on one of the two shafts in the frame makes a pivotal movement during which the force opposing this movement remains substantially constant. Even if the user of the instrument would keep moving the handle downwardly after reaching this adjusted force, this movement only results in a relative pivotal movement between the needle holder and the handle without substantially changing the force applied on the bottom of the periodontal cavity by the probe needle. In practice, a pivotal movement of the needle holder with respect to the center line of the handle in the order of 45° is sufficient.

Although the allowable probe needle pressure can thus be accurately maintained very constant, the construction with the Tensator spring is, however, complex, expensive and voluminous, which obstructs the view which should be seen as a disadvantage in view of the place at which the measuring instrument is used. Further, after contamination of the wound springs good operation of the measuring instrument cannot be guaranteed and sterilizing such a Tensator spring construction is not simple. As already mentioned, the chosen spring construction is derived from the Tensator motor which is designed for transferring a constant torque over many shaft rotations and, therefore, unnecessarily complicated for a measuring instrument of the present kind wherein an angle rotation of one axis over a maximum of 60° is necessary.

SUMMARY OF THE INVENTION

Starting from the fact that although an accurate depth measurement of the periodontal pocket cavity is desired, depth variations will, however, occur for each pocket cavity and, therefore, an accuracy of 0.5 mm will be sufficient for the daily practice. The invention aims to provide a measuring instrument of the above-mentioned kind, which is constructively simpler, which is compact and thereby simpler to use and which can be manufactured relatively inexpensively and further, can be more easily sterilized.

To this end, according to the invention the needle holder and the handle each are attached to parts of a hinge, and the hinge parts are biased to the closed position of the hinge by a spring with a spring characteristic which is substantially flat at least within the restricted pivoting range of the hinge.

Such a hinge can be made compact and especially flat, whereby the user of the instrument has a good view on the probe position under all circumstances. The invention is based on the principle that a substantially constant spring force opposing the probe needle movements can also be obtained with constructively simple spring means provided that a spring design is used, wherein the restricted spring deformations at least within the range determined by the restricted needle movements cause no substantial variations of the spring force.

There are several spring designs having a mainly flat characteristic within the above defined restricted pivoting range, i.e. a characteristic extending mainly parallel with the spring path axis of a force-path diagram.

According to the invention the bias spring can be a helical spring extending in the hollow handle. By using the space in the handle in this manner, especially the length of this space, the bias spring may have a great length, at least a longitudinal dimension which is great in relation to the spring deformation caused by the needle pivoting movement.

According to another embodiment of the invention the bias spring can be a mainly omega-shaped leaf spring, the ends of which engage the respective hinge parts at both sides of the hinge axis. Such an omega-shaped leaf spring can be made compact and be accommodated in a space formed in the hinge parts for this purpose.

In principle, the bias spring can also be a volute spring, i.e. a leaf spring consisting of two oppositely wound spiral parts connected by a bridge, the facing circumferential zones of which spiral parts apply a clamping force on the hinge parts lying therebetween, which force is substantially independent of the deformation of the spring. The spiral spring parts are not attached to any axis and when the spiral parts move away from each other because of the probe needle movement, the bridge will be distorted in such a manner that the radius of curvature thereof increases. In reaction to this the spiral spring parts will unroll whereby the bridge is in fact lengthened, which results in a substantially constant clamping force.

Another type of spring with a substantially flat section in the characteristic is a helical spring loaded on flexure by the moving hinge parts.

BRIEF DESCRIPTION OF THE DRAWINGS

The invention will hereinafter be further explained by reference to the drawings showing some embodiments of the measuring instrument for the depth of the periodontal cavity.

FIGS. 1A and 1B show a first embodiment of the measuring instrument in the closed unloaded state and the opened loaded state, respectively;

FIG. 2 is a longitudinal section of the measuring instrument according to FIGS. 1A and 1B;

FIGS. 3, 4 and 5 schematically show some alternative embodiments of the measuring instrument with several types of bias springs.

DETAILED DESCRIPTION OF THE PREFERRED EMBODIMENTS

The measuring instrument according to the invention comprises a handle 1 having opposite proximal and distal ends, a probe needle 2 and a needle holder 3. The probe needle may be provided with a graduation for reading the measured depth of a periodontal cavity in a known manner.

According to the invention the handle 1 and the needle holder 3 each are attached to a part of a hinge 4, which hinge parts 5 and 6 are interconnected by a hinge axis 7.

In the embodiment according to FIGS. 1A, 1B and 2, the hinge parts 5 and 6 are biased to the closed position of FIGS. 1A by a draw or extension spring 8, an end of which is connected with the hinge part 6 by means of a flexible wire 9, while the other end may be attached to the end of the handle opposite to the hinge 4; however, the end of the spring 8 is preferably connected with an adjusting mechamism for the bias force consisting of a screw bushing construction 11 and an operating knob 10. In view of the relatively great length of the spring 8 the spring deformation at the transition from the situation of FIG. 1A to the situation of FIG. 1B will be so low that a mainly linear and flat spring characteristic will be obtained. Therefore, the force applied to the tip of the needle 2 will be substantially constant during the pivoting movement of the hinge part 6 away from the hinge part 5, as soon as this force has reached the value for stretching the spring 8. The hinge axis 7 is displaced transversely of the handle axis, but is aligned with the probe holder axis; the distal end of spring 9 is attached to hinge part 6 at a point transversely displaced from said hinge axis.

The hinge 4 can be made relatively compact and flat, so that the view of the operator of the instrument on the position where the probing is executed is not or substantially not restricted. Further, the sterilizing of the measuring instrument can be done thoroughly in a simple manner.

By using a flexible connection wire 9 between the spring 8 and the hinge part 6, the path of the wire 9 can be bent without a noticeable influence on the characteristic of the spring 8. Therefore, the hinge axis 7 can be in line with the center line of the handle 1, for example by giving the handle 1 a curvature as shown in FIG. 1B by a dotted line, if this is desired for some reason.

FIG. 3 shows an embodiment, wherein an omega-shaped leaf spring 12 is used, the ends of which are connected with the respective hinge parts 5 and 6, and the spring's intermediate part is generally adjacent and bridging the hinge axis 7.

FIG. 4 schematically shows an embodiment wherein a volute spring 13 is used for biasing, and FIG. 5 shows an embodiment wherein a helical spring 14 loaded on flexure is used for biasing. FIGS. 3, 4 and 5 only show an operating principle by using specific springs. It will be clear that the springs 12, 13 and 14 can be accommodated entirely or partially in spaces formed in a hinge of the type shown in FIG. 1.

It is noted that the measuring instrument according to the invention can also be used for medical or paramedical purposes, wherein a constant measuring pressure is required.

I claim:

1. An instrument for measuring the depth of a periodontal cavity comprising:
    a probe needle,
    a holder in which said needle is securable,
    a handle,
    a hinge having first and second hinge parts attached to said holder and handle respectively and pivot-means about which said parts are pivotally connected to each other,
    a spring having opposite ends engaged to said hinge parts respectively and an intermediate part situated generally adjacent and bridging said pivot means, said spring adapted to bias said hinge parts to a closed position of said hinge, said spring having a substantially flat spring characteristic at least within the pivoting range of said hinge,
    said needle and holder therefor being pivotable relative to said handle only when a predetermined force sufficient to overcome said spring is exerted on said needle relative to said handle.

2. An instrument according to claim 1 wherein said spring comprises a generally omega-shaped leaf spring having opposite ends which are secured respectively to said first and second hinge parts.

3. An instrument according to claim 1 wherein said spring comprises a volute leaf spring having two oppositely wound spiral parts connected by a bridge, said spiral parts having facing circumferential zones which engage and apply a clamping force on said hinge parts situated therebetween.

4. An instrument according to claim 1 wherein said spring comprises an elongated helical spring having opposite ends which are secured respectively to said first and second hinge parts.

5. An instrument according to claim 1 wherein said needle has a pointed tip end and includes indicia thereon along its length beginning at said tip end to indicate the depth to which said needle end has penetrated.

6. An instrument for measuring the depth of a periodontal cavity comprising:
    a probe needle,
    a holder in which said probe needle is securable,
    an elongated handle having an elongated cavity therein, proximal and distal ends, and a central axis,
    a hinge having first and second parts attached to said holder and handle's distal end respectively, and pivot means about which said first and second parts are privotally connected to each other, said pivot means being transversely displaced from said handle axis
    an elongated spring situated in said handle cavity, said spring having opposite ends, one secured in and to said handle, the other extending out of said distal end and secured to said first part of the hinge at a point transversely displaced from said hinge axis, said spring adapted to bias said hinge parts to a closed position of said hinge, said spring having a substantially flat spring characteristic at least within the pivoting range of said hinge,
said needle and holder therefor being pivotable relative to said handle only when a predetermined force sufficient to overcone said spring is exerted on said needle relative to said handle.

* * * * *